(12) United States Patent
Xu et al.

(10) Patent No.: US 10,525,164 B2
(45) Date of Patent: Jan. 7, 2020

(54) VASCULAR GRAFTS DERIVED FROM ACELLULAR TISSUE MATRICES

(75) Inventors: Hui Xu, Plainsboro, NJ (US); Cunqi Cui, Plainsboro, NJ (US); Joshua Czeczuga, Brick, NJ (US); Jared Lombardi, Somerset, NJ (US)

(73) Assignee: LifeCell Corporation, Madison, NJ (US)

(*) Notice: Subject to any disclaimer, the term of this patent is extended or adjusted under 35 U.S.C. 154(b) by 713 days.

(21) Appl. No.: 12/862,033

(22) Filed: Aug. 24, 2010

(65) Prior Publication Data

US 2011/0054588 A1 Mar. 3, 2011

Related U.S. Application Data

(60) Provisional application No. 61/239,237, filed on Sep. 2, 2009.

(51) Int. Cl.
*A61L 27/36* (2006.01)
*A61L 27/50* (2006.01)
*A61F 2/06* (2013.01)

(52) U.S. Cl.
CPC ............ *A61L 27/3604* (2013.01); *A61F 2/06* (2013.01); *A61L 27/507* (2013.01); *A61L 2430/36* (2013.01); *Y10T 156/1002* (2015.01)

(58) Field of Classification Search
CPC ...... A61F 2/06; A61F 2/04; A61F 2/07; A61F 2/02; A61L 31/16; A61L 27/507
USPC ......................... 623/1.44, 23.64, 23.7, 23.71
See application file for complete search history.

(56) References Cited

U.S. PATENT DOCUMENTS

| | | | |
|---|---|---|---|
| 3,995,641 A | | 12/1976 | Kronenthal et al. |
| 4,740,534 A | | 4/1988 | Matsuda et al. |
| 4,759,764 A | | 7/1988 | Fawcett et al. |
| 4,776,853 A | * | 10/1988 | Klement et al. ............... 8/94.11 |
| 4,902,508 A | * | 2/1990 | Badylak et al. .............. 424/423 |
| 5,019,087 A | | 5/1991 | Nichols |
| 5,584,855 A | | 12/1996 | Seckel |
| 5,762,600 A | * | 6/1998 | Bruchman ............ A61L 27/507 600/36 |
| 5,834,029 A | | 11/1998 | Bellamkonda et al. |
| 6,099,567 A | | 8/2000 | Badylak et al. |
| 6,166,288 A | | 12/2000 | Diamond et al. |

(Continued)

FOREIGN PATENT DOCUMENTS

| | | |
|---|---|---|
| CN | 1927413 A | 3/2007 |
| EP | 0 390 481 A2 | 10/1990 |

(Continued)

OTHER PUBLICATIONS

Wengerter, et al, Semin Vasc Surg, 1999, 12(1):46-51. (Abstract Only).*

(Continued)

*Primary Examiner* — Leslie Lopez
(74) *Attorney, Agent, or Firm* — McCarter & English, LLP; Matthew R. Van Eman; George Blazeski

(57) ABSTRACT

A vascular graft for treatment of diseased or damaged blood vessels is disclosed. The graft comprises a sheet of acellular tissue matrix with an intact basement membrane. The graft is formed by wrapping the sheet into a tube and securing the edges of the sheet together. The acellular tissue matrix facilitates tissue ingrowth and remodeling of the graft with host cells.

8 Claims, 13 Drawing Sheets

(56) References Cited

U.S. PATENT DOCUMENTS

| | | | |
|---|---|---|---|
| 6,331,319 B1 | 12/2001 | Badylak et al. | |
| 6,358,284 B1* | 3/2002 | Fearnot et al. | 623/23.72 |
| 6,371,992 B1 | 4/2002 | Tanagho et al. | |
| 6,416,995 B1 | 7/2002 | Wolfinbarger | |
| 6,432,712 B1 | 8/2002 | Wolfinbarger, Jr. | |
| 6,918,396 B1 | 7/2005 | Badylak et al. | |
| 6,986,735 B2 | 1/2006 | Abraham et al. | |
| 6,991,813 B2* | 1/2006 | Xu | 424/725 |
| 2002/0055769 A1* | 5/2002 | Wang | A61F 2/82 623/1.13 |
| 2003/0018378 A1* | 1/2003 | Sarac | 623/1.13 |
| 2003/0035843 A1* | 2/2003 | Livesey et al. | 424/549 |
| 2003/0167088 A1* | 9/2003 | Abraham et al. | 623/1.41 |
| 2004/0158320 A1* | 8/2004 | Simionescu | A61F 2/2412 623/2.14 |
| 2005/0013870 A1* | 1/2005 | Freyman | A61L 27/3633 424/520 |
| 2005/0028228 A1 | 2/2005 | McQuillan et al. | |
| 2005/0222661 A1* | 10/2005 | Case et al. | 623/1.1 |
| 2007/0004961 A1 | 1/2007 | Case et al. | |
| 2007/0207125 A1* | 9/2007 | Bothwell et al. | 424/93.7 |
| 2007/0260109 A1* | 11/2007 | Squillace | A61L 2/0088 600/36 |
| 2007/0293937 A1* | 12/2007 | Biggs et al. | 623/1.13 |
| 2007/0298070 A1 | 12/2007 | Van Dyke | |
| 2008/0171092 A1 | 7/2008 | Cook et al. | |

FOREIGN PATENT DOCUMENTS

| | | |
|---|---|---|
| WO | 90/00395 A1 | 1/1990 |
| WO | 95/29714 A1 | 11/1995 |
| WO | 03/032735 A1 | 4/2003 |
| WO | WO 03/092471 A2 | 11/2003 |
| WO | 2005/009134 A1 | 2/2005 |
| WO | WO 2005/023321 A2 | 3/2005 |
| WO | WO-2005/023321 A2 | 3/2005 |
| WO | 2005/089411 A2 | 9/2005 |

OTHER PUBLICATIONS

Ballermann, B.J. "Adding Endothelium to Artificial Vascular Grafts" *News Physiol. Sci.* 13:154 (Jun. 1998).

Bellamkonda, R.V. "Peripheral nerve regeneration: An opinion on channels, scaffolds and anisotropy" *Biomaterials* 27:3515-3518 (2006).

Caplan, A.I. "The Mesengenic Process" *Clin. Plast. Surg.* 21(3):429-435 (1994).

Caplan, A.I. et al. "Principles of Cartilage Repair and Regeneration" *Clin. Orthop. Rel. Res.* 342:254-269 (1997).

Caplan, A.I. "Mesenchymal Stem Cells" *J. Orthop. Res.* 9:641-650 (1991).

Collins, B. H. et al. "Cardiac Xenografts Between Primate Species Provide Evidence for the Importance of the α-Galactosyl Determinant in Hyperacute Rejection" *J. Immunol.* 154:5500-5510 (1995).

Galili, U. et al. "Interaction of the natural anti-Gal antibody with a-galactosyl epitopes: a major obstacle for xenotransplantation in humans" *Immunology Today* 14(10):480-482 (1993).

Galili, U. et al. "Interaction between Human Natural Anti-α-Galactosyl Immunoglobulin G and Bacteria of the Human Flora" *Infect. Immun.* 56(7):1730-1737 (Jul. 1988).

Galili, U. et al. "Man, Apes, and Old World Monkeys Differ from Other Mammals in the Expression of α-Galactosyl Epitopes on Nucleated Cells" *J. Biol. Chem.* 263(33):17755-17762 (1988).

Good, A. H. et al. "Identification of Carbohydrate Structures That Bind Human Antiporcine Antibodies: Implications for Discordant Xenografting in Humans" *Transplant. Proc.* 24(2):559-562 (1992).

Hamadeh, R.M. et al. "Human Natural Anti-Gal IgG Regulates Alternative Complement Pathway Activation on Bacterial Surfaces" *J. Clin. Invest.* 89:1223-1235 (1992).

Katayama, Y. et al. "Coil-reinforced hydrogel tubes promote nerve regeneration equivalent to that of nerve autografts" *Biomaterials* 27:505-518 (2006).

Kemp, S.W. et al. "Collagen nerve conduits promote enhanced axonal regeneration, schwann cell association, and neovascularization compared to silicone conduits" *Tissue Eng Part A* 15(8):1975-1988 (Aug. 2009).

L'Heureux, N. et al. "Human tissue-engineered blood vessels for adult arterial revascularization" *Nature Medicine* 12(3):361-365 (Mar. 2006).

McNally, K.M. et al. "Improved vascular tissue fusion using new light-activated surgical adhesive on a canine model" *J. Biomed. Opt.* 6(1):68-73 (Jan. 2001).

Sandrin, M.S. et al. "Anti-pig IgM antibodies in human serum react predominantly with Gal(α1-3)Gal epitopes" *Proc. Natl. Acad. Sci. USA* 90:11391-11395 (1993).

Terzis, J.K. et al. "Vein Grafts Used as Nerve Conduits for Obstetrical Brachial Plexus Palsy Reconstruction" *Plast. Reconstr. Surg.* 120(7):1930-1941 (2007).

Wang, X. et al. "Development of Small-Diameter Vascular Grafts" *World J. Surg.* 31:682-689 (2007).

Williams, L.R. "Rat Aorta Isografts Possess Nerve Regeneration-Promoting Properties in Silicone Y Chambers" *Experimental Neurology* 97:555-563 (1987).

Xu, H. et al. "A porcine-derived acellular dermal scaffold that supports soft tissue regeneration: removal of terminal galactose-alpha-(1,3)-galactose and retention of matrix structure" *Tissue Eng Part A* 15(7):1807-1819 (Jul. 2009).

Zhong, H. et al. "Nerve Regeneration and Functional Recovery after a Sciatic Nerve Gap Is Repaired by an Acellular Nerve Allograft Made through Chemical Extraction in Canines" *J. Reconstr. Microsurg.* 23(8):479-487 (2007).

International Search Report and Written Opinion for PCT/US2010/046478 dated May 18, 2011, from the International Searching Authority of the European Patent Office.

Schaner, P.J. et al., "Decellularized vein as a potential scaffold for vascular tissue engineering", *J Vasc Surg*, 2004:40:pp. 146-153.

Chen, F, et al., "Acellular Collagen Matrix as a Possible 'Off the Shelf' Biomaterial for Urethral Repair", *Urology*, vol. 54 (3), 1999, pp. 407-410.

Huynh, T., et al., "Remodeling of an acellular collagen graft into a physiologically responsive neovessel", *Nature Biotechnology*, vol. 17, Nov. 1999, pp. 1083-1086.

Lu, Q. et al., "Novel porous aortic elastin and collagen scaffolds for tissue engineering", *Biomaterials*, vol. 25 (2004), pp. 5227-5237.

Tsai, John W., et al., "Permacol (Porcine Dermal Collagen) and Alloderm (Acellular Cadaveric Dermis) as a Vascular Patch Repair for Common Carotid Arteriotomy in a Rabbit Model," Basic Science Research, vol. 23, No. 3, May 2009, pp. 374-381.

Brown, et. al., "The Basement Membrane Component of Biological Scaffolds Derived from Extracellular Matrix," Tissue Engineering, Mar. 2006, vol. 12, No. 3: 519-526.

European Search Report; Search Completion Date: Oct. 30, 2014 for EP Application No. 13198645, 4 pages.

* cited by examiner

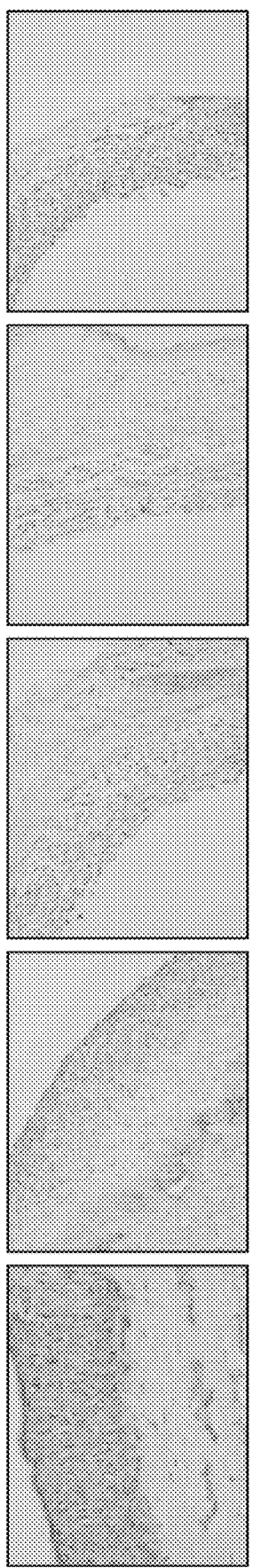
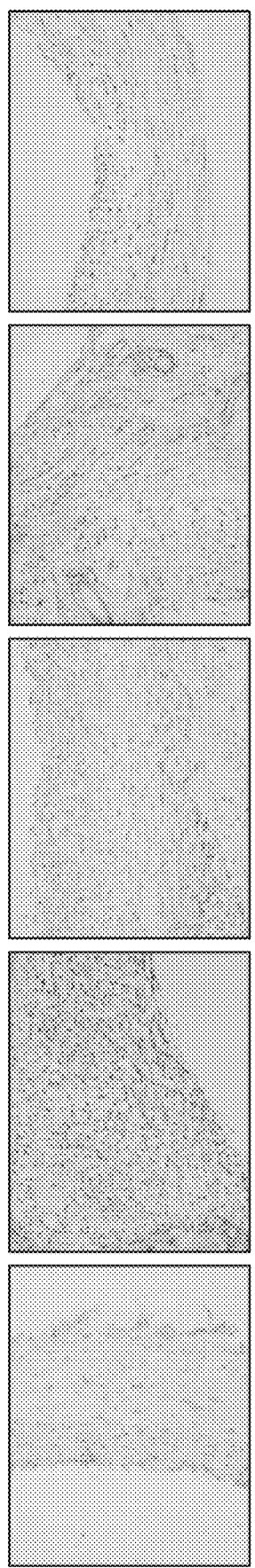
FIG. 9A  FIG. 9B  FIG. 9C  FIG. 9D  FIG. 9E
FIG. 9F  FIG. 9G  FIG. 9H  FIG. 9I  FIG. 9J

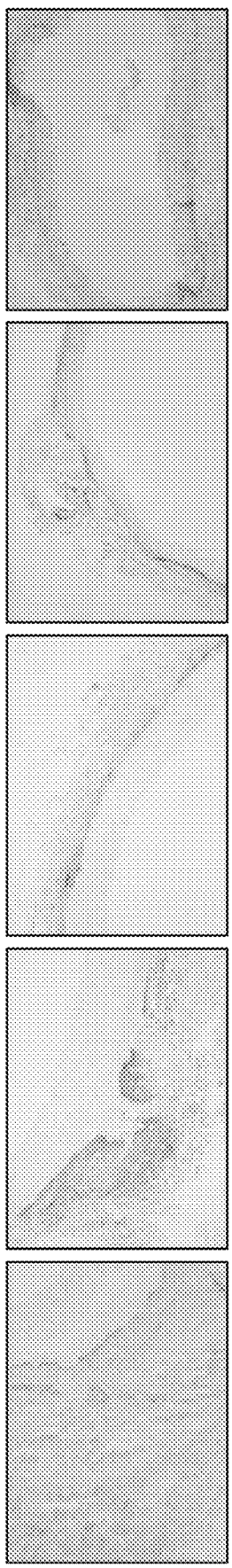 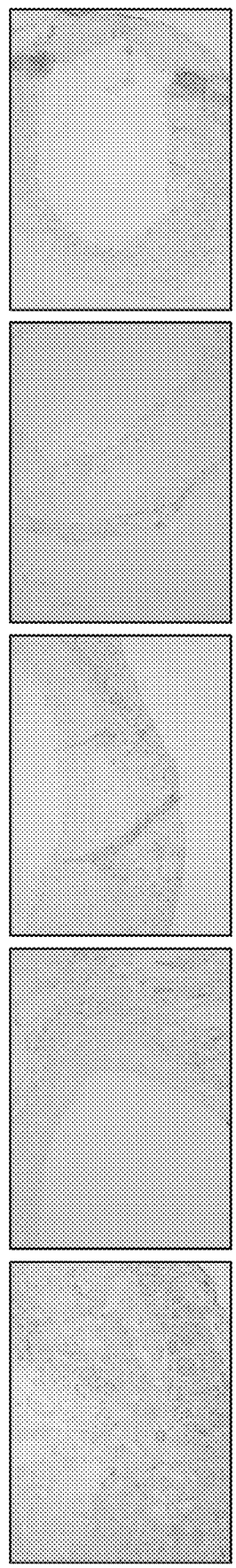
FIG. 11A FIG. 11B FIG. 11C FIG. 11D FIG. 11E
FIG. 11F FIG. 11G FIG. 11H FIG. 11I FIG. 11J

VASCULAR GRAFTS DERIVED FROM ACELLULAR TISSUE MATRICES

This application claims priority to U.S. Provisional Application No. 61/239,237, filed Sep. 2, 2009, which is incorporated herein by reference in its entirety.

The present disclosure relates generally to vascular grafts, and more specifically, to vascular grafts derived from acellular tissue matrices and methods of producing the grafts.

Recent advancements in the field of bioengineering and cardiovascular research have lead to the development of new techniques and materials for constructing vascular conduits for bypass surgery, repair of damaged or diseased blood vessels, and other vascular procedures. Vascular grafts include a wide variety of synthetic and biological constructs.

Despite developments in graft technology, the repair or replacement of vascular structures continues to remain challenging, particularly due to the complications resulting from synthetic graft use, such as enteric fistulae formation, distal embolization, graft infection and occlusion, limited durability, and lack of compliance of the graft around the anastomosis, thus necessitating further intervention. The application of autografts for vascular replacement is hindered by the dimensional limitation of the harvested grafts, donor site morbidity and surgical costs associated with the harvest of autologous vessels. Additionally, a significant number of patients do not have veins suitable for grafting due to preexisting vascular disease, vein stripping or prior vascular procedures.

The present disclosure provides improved methods and materials for construction of vascular grafts.

In one aspect of the present disclosure, a vascular graft for treatment of a diseased or damaged blood vessel is provided. The vascular graft comprises a tubular conduit comprising a tubular wall that is impervious to blood and defining a lumen for the passage of blood there through. The tubular wall comprises a sheet of acellular tissue matrix having a basement membrane. The basement membrane forms a luminal surface of the tubular conduit.

In another aspect of the present disclosure, a method of forming a vascular graft is provided. The method comprises the steps of providing a sheet of acellular tissue matrix having a basement membrane, and forming the sheet into a tubular conduit. The basement membrane forms an inner luminal surface of the tubular conduit.

It is to be understood that both the foregoing general description and the following detailed description are exemplary and explanatory only and are not restrictive of the invention, as claimed.

The accompanying drawings, which are incorporated in and constitute a part of this specification, illustrate methods and embodiments of the invention and together with the description, serve to explain the principles of the various aspects of the invention.

BRIEF DESCRIPTION OF DRAWINGS

FIGS. 9A-9E are images of histological sections of explanted vascular grafts stained with antibodies against smooth muscle cells, as described in Example 1;

FIGS. 9F-9J are images of histological sections of explanted vascular grafts stained with antibodies against fibroblast cells, as described in Example 1;

FIGS. 11A-11E are images of histological sections of explanted vascular grafts stained with antibodies against rat IgG, as described in Example 1;

FIGS. 11F-11J are images of histological sections of explanted vascular grafts stained with antibodies against rat IgM, as described in Example 1;

DESCRIPTION OF EXEMPLARY EMBODIMENTS

Figure 1A:
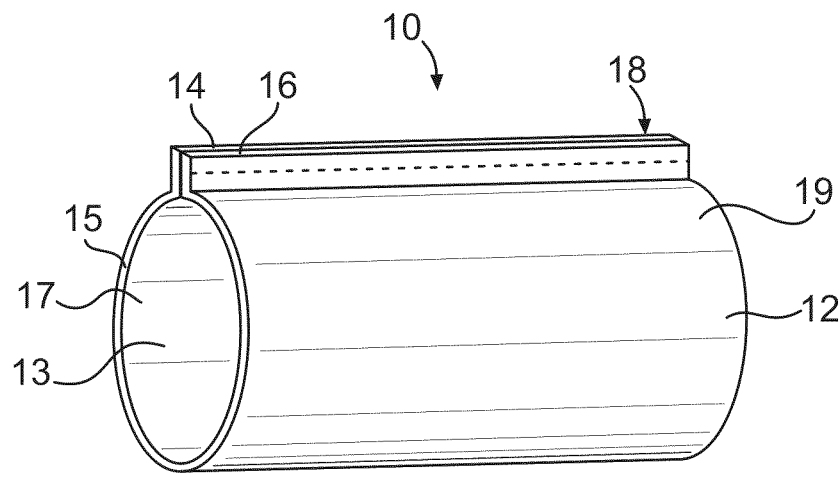
FIG. 1A shows an exemplary embodiment of a vascular graft for treatment of a diseased or damaged blood vessel.

Reference will now be made in detail to certain embodiments consistent with the present disclosure, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit, unless specifically stated otherwise. Also the use of the term "portion" may include part of a moiety or the entire moiety.

The term "acellular tissue matrix," as used herein, refers generally to any tissue matrix that is substantially free of cells and other antigenic material. In various embodiments, acellular tissue matrices derived from human or xenogenic sources may be used to produce the scaffolds. Skin, parts of skin (e.g., dermis), and other tissues such as blood vessels, heart valves, fascia and nerve connective tissue may be used to create acellular matrices to produce tissues scaffolds within the scope of the present disclosure.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

In various embodiments, materials and methods for construction of arterial or venous grafts for treatment of blood vessel defects are provided. In various embodiments, the vascular grafts are used for replacement of a portion of a diseased or damaged blood vessel, for example, replacement of a weakened portioned of the aorta, treatment of damaged vessels due to trauma, treatment of vascular diseases caused by medical conditions (e.g. diabetes, autoimmune disease, etc.). In some embodiments, the vascular grafts are used for bypassing and/or replacing stenotic or partially occluded segments of a blood vessel, for example, coronary and peripheral artery bypass grafting.

In some embodiments, a vascular graft comprises a sheet of material formed into a tubular conduit. The tubular wall of the graft is impermeable to blood under hemodynamic pressures experienced by native blood vessels. In various embodiments, the material sheet forming the tubular graft has sufficient strength and durability for use in vascular applications, and the mechanical properties (e.g., elasticity) are similar to those of the adjacent host vessel. In certain embodiments, the luminal lining of the graft is antithrombotic. In some embodiments, the material sheet forming the graft supports tissue remodeling and repopulation of the graft with the host cells. In certain embodiments, the material forming the graft supports endothelial cell deposition on the luminal surface and smooth muscle cell integration into the tubular wall of the graft.

A basement membrane is a thin sheet of extracellular material contiguous with the basilar aspect of epithelial cells. Sheets of aggregated epithelial cells form an epithelium. Thus, for example, the epithelium of skin is called the epidermis, and the skin basement membrane lies between the epidermis and the dermis. The basement membrane is a specialized extracellular matrix that provides a barrier function and an attachment surface for epithelial-like cells; however, it does not contribute any significant structural or biomechanical role to the underlying tissue (e.g., dermis). Components of basement membranes include, for example, laminin, collagen type VII, and nidogen. The temporal and spatial organizations of the epithelial basement membrane distinguish it from, e.g., the dermal extracellular matrix.

In some embodiments, the sheet of material may include an acellular tissue matrix. In various embodiments, the acellular tissue matrix comprises an intact basement membrane. In some embodiments, the basement membrane forms the luminal surface of the vascular conduit. The basement membrane provides a continuous, non-porous luminal surface to the graft, and thereby, prevents leakage of blood from the lumen of the graft. In addition, the basement membrane may support growth of endothelial cells and prevent thrombosis. The basement membrane may, therefore, allow formation of an endothelial lining that prevents leakage and/or thrombosis, but does not require seeding or culture with exogenous cells.

The acellular tissue matrix can be formed from a number of different tissues that include a basement membrane. For example, the acellular tissue matrix can be formed from skin, urinary bladder, intestine, pericardial tissue, peritoneum or combinations of tissues. One biomaterial suitable for forming the acellular matrix is derived from human skin, such as ALLODERM®, which is available from (LifeCell Corp, Branchburg, N.J.). ALLODERM® is a human acellular dermal matrix that has been processed to remove both the epidermis and the cells that can lead to tissue rejection and graft failure, without damaging the dermal proteins and the basement membrane. In another exemplary embodiment, the acellular tissue matrix comprises a pericardial matrix generated by processing pericardial tissue while maintaining the integrity of the basement membrane. In yet another embodiment, the acellular tissue matrix is derived from peritoneal membrane, which is processed to remove the cells while keeping the basement membrane intact. Production of suitable acellular tissue matrices is described in more detail below.

In various embodiments, the luminal surface of the graft is modified using anti-thrombotic and/or anti-calcification agents to inhibit graft occlusion after surgery. In other embodiments, the luminal surface of the vascular graft is treated with growth factors that enhance proliferation of endothelial cells along the luminal surface.

To form a sheet of acellular tissue matrix into a tube, opposing edges of the sheet may be attached to one another. In various embodiments, the edges are attached to one another using sutures, a biologically compatible adhesive, or a combination of both, to form a fluid-tight seam extending longitudinally along the length of the graft. In some embodiments, the edges of the rolled sheet are secured using heat and pressure treatment. Suitable sutures include, for example, polypropylene sutures (PROLENE®), and can be continuous or interrupted. Suitable adhesives include, for example, fibrin glue, cyanoacrylate-based tissue adhesives (e.g., DERMABOND®), and chitosan tissue adhesives. In some embodiments, the edges of the sheet are crosslinked (e.g., using chemical or radiation induced cross-linking) to each other or to an underlying layer of material to ensure that the edges do not come loose after the sheet is rolled in a tubular construct.

Figure 1B:
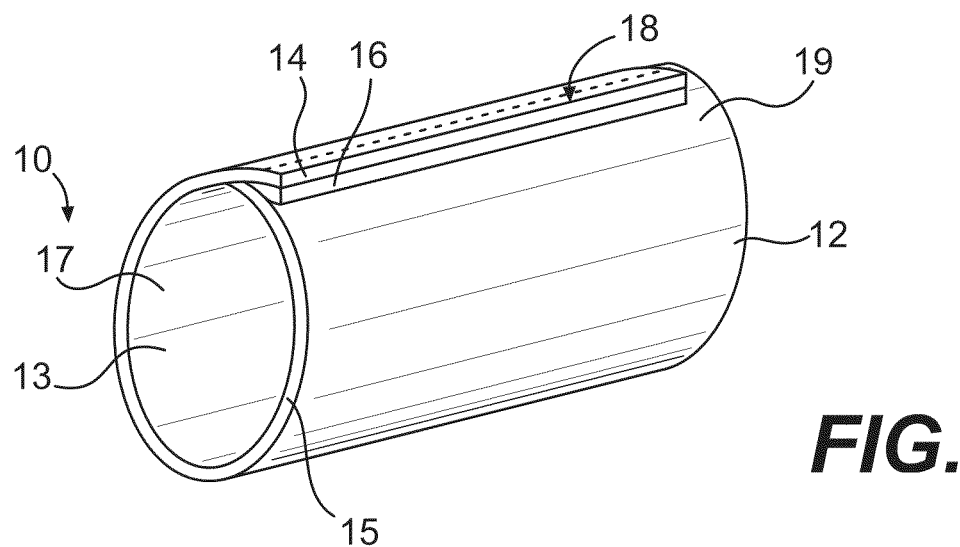
FIG. 1B shows an alternate configuration of the vascular graft depicted in FIG. 1.

FIG. 1A shows an exemplary embodiment of a vascular graft 10 in accordance with the present disclosure. Graft 10 comprises a sheet of material 12 that is rolled into a tubular construct defining a lumen 13 and a tubular wall 15 having a luminal surface 17 and abluminal surface 19. Longitudinal edges 14, 16 of the sheet are brought into contact with each other on the abluminal side of the tubular construct, and are attached using surgical sutures and/or bioadhesives along the length of the graft. The attachment of the longitudinal edges 14, 16 creates a longitudinal ridge 18 that protrudes above abluminal surface 19 and extends along the length of the tubular graft. In one embodiment, longitudinal ridge 18 is folded and attached to the abluminal surface 19 of graft 10, as shown in FIG. 1B. Longitudinal ridge 18 is secured to tubular wall 15 along the length of the graft using sutures, adhesives, or a combination of both.

Figure 2A:
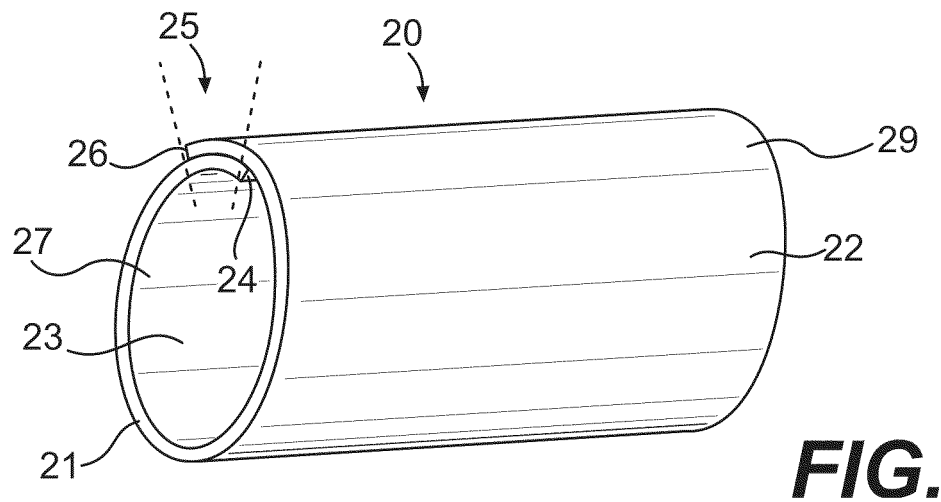
FIG. 2A shows another exemplary embodiment of a vascular graft for treatment of a diseased or damaged blood vessel.

FIG. 2A shows an exemplary embodiment of a vascular graft 20 in accordance with the present disclosure. Graft 20 comprises a sheet of material 22 that is rolled into a tubular structure defining a lumen 23. The sheet of material 22 forms a tubular wall 21 having a luminal surface 27 and an abluminal surface 29. The sheet 22 comprises a first longitudinal edge 24 and a second longitudinal edge 26 at opposite ends of the sheet 22. When the sheet 22 is rolled into a tube, second longitudinal edge 26 extends over first edge 24 to define a multi-layered overlapped region 25 extending between first edge 24 and second edge 26. The overlapped region 25 is sealed along the length of the graft using sutures and/or adhesives. In certain embodiments, the range of overlap is at least 10% of the width of an individual sheet of material.

Suitable vascular grafts can be formed using a number of techniques. Generally, grafts will be produced based on a desired size, length, and biomechanical requirements needed for a selected implant location. For example, a graft intended for use as an aortic vascular graft will generally have a size and biomechanical properties (e.g., burst strength) that are higher than those for other location, which may experience lower pressures and carry less blood flow.

In various embodiments, the thickness of the sheet of material is consistent with the wall thickness of a blood vessel to be replaced by the vascular graft. In certain embodiments, the sheet of material is sized to correspond to the wall thickness of a native blood vessel.

Figure 2B:
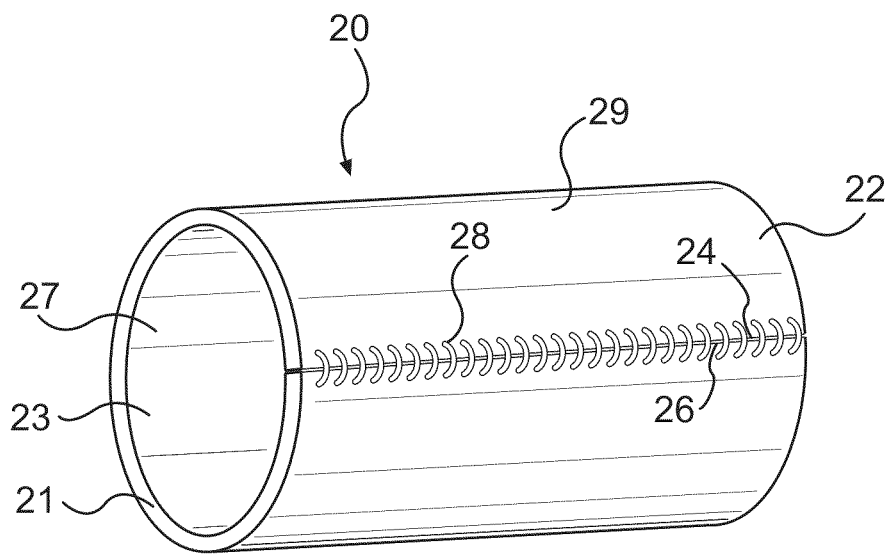
FIG. 2B shows yet another exemplary embodiment of a vascular graft for treatment of a diseased or damaged blood vessel.
Figure 3:
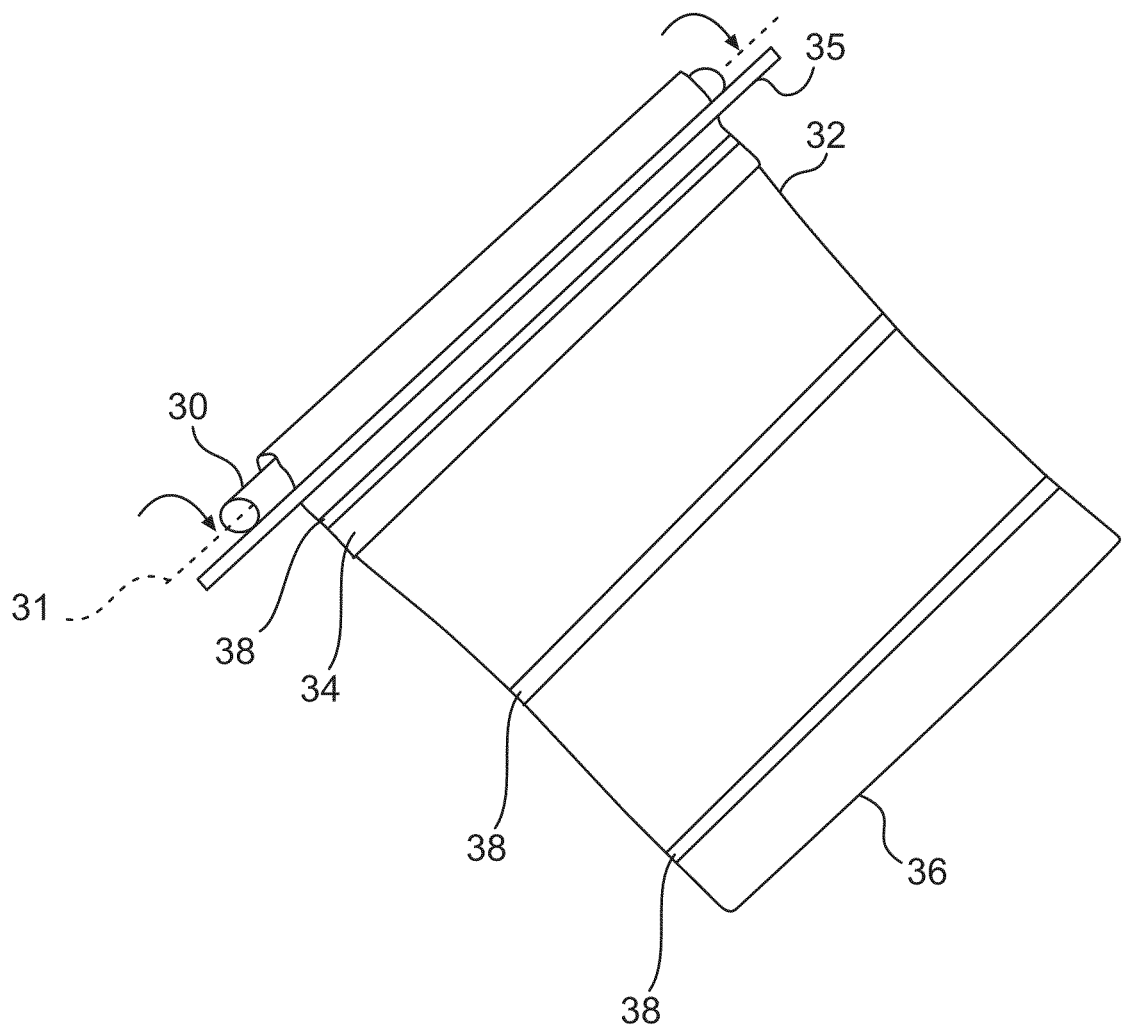
FIG. 3 illustrates a method of forming a vascular graft according to certain embodiments.

In some embodiments, grafts can be formed by rolling a sheet of material to a predetermined size (i.e. luminal diameter). In some embodiments, as illustrated in FIG. 2, a vascular graft can be formed by wrapping a sheet of biomaterial 32 around the exterior surface of a cylindrical rod or tube 30. A longitudinal section 34 of the sheet is folded around a cylindrical rod 30. In one embodiment, a locking rod 35 is positioned parallel to the cylindrical rod 30, as shown in FIG. 3, to lock section 34 against the cylindrical rod. A suture held taut between two holders can also be used to lock section 34 against the cylindrical rod. The rod is then rolled at least 360° about a longitudinal axis 31 of the rod to wrap the sheet of material around the exterior surface of the rod. In one embodiment, sheet 32 is wrapped around the rod multiple times to form a multi-layered graft. After the sheet is wound around the cylindrical rod, the outer edge 36 of the sheet is secured to an underlying layer of sheet, as illustrated in FIG. 2.

In one embodiment, adhesive strips 38 are attached to sheet 32 on multiple locations across the width of the sheet, as shown in FIG. 3. In such an embodiment, adhesive strips 38 bind the sheet 32 to an underlying layer of material as the sheet is wrapped around the cylindrical rod 30.

The inner diameter of the tubular graft is substantially equal to the outer diameter of cylindrical rod or tubing 30. Therefore, the diameter of the rod or tube is selected to match the luminal diameter of the native blood vessel to be replaced by the graft construct. In one embodiment, the diameter of the rod is approximately between 4-5 mm, which is used for constructing small-diameter (<6 mm) vascular grafts. In another embodiment, the wall thickness of the tube is 1 mm. After the sheet is wrapped around the rod and the longitudinal edge(s) of the sheet are secured, the rod is withdrawn from within the rolled sheet. In another embodiment, the tubing is stretch longitudinally to slide the sheet off of the tubing. The material of the cylindrical rod is selected to inhibit attachment of the sheet to the exterior surface of the rod. In one exemplary embodiment, the cylindrical rod used is a glass rod. In another embodiment, the cylindrical tube used is a rubber tube. In yet another embodiment, the tube used is a silicone tube Suitable Acellular Tissue Matrices In some embodiments, suitable acellular tissue matrices may, for example, retain certain biological functions, such as cell recognition, cell binding, the ability to support cell spreading, cell proliferation, cellular in-growth and cell differentiation. Such functions may be provided, for example, by undenatured collagenous proteins (e.g., type I collagen) and a variety of non-collagenous molecules (e.g., proteins that serve as ligands for either molecules such as integrin receptors, molecules with high charge density such as glycosaminoglycans (e.g., hyaluronan) or proteoglycans, or other adhesins). In some embodiments, the acellular tissue matrices may retain certain structural functions, including maintenance of histological architecture and maintenance of the three-dimensional array of the tissue's components. The acellular tissue matrices described herein may also, for example, exhibit desirable physical characteristics such as strength, elasticity, and durability, defined porosity, and retention of macromolecules. Suitable acellular tissue matrices may be crosslinked or uncrosslinked.

In some embodiments, the graft material is amenable to being remodeled by infiltrating cells, such as differentiated cells of the relevant host tissue, stem cells such as mesenchymal stem cells, or progenitor cells. This may be accomplished, for example, by forming the grafted matrix material from tissue that is identical to the surrounding host tissue, but such identity is not necessary.

Remodeling may be directed by the above-described acellular tissue matrix components and signals from the surrounding host tissue (such as cytokines, extracellular matrix components, biomechanical stimuli, and bioelectrical stimuli). For example, the presence of mesenchymal stem cells in the bone marrow and the peripheral circulation has been documented in the literature and shown to regenerate a variety of musculoskeletal tissues [Caplan (1991) J. Orthop. Res. 9:641-650; Caplan (1994) Clin. Plast. Surg. 21:429-435; and Caplan et al. (1997) Clin Orthop. 342:254-269]. Additionally, the graft should provide some degree (greater than threshold) of tensile and biomechanical strength during the remodeling process.

Acellular tissue matrices may be manufactured from a variety of source tissues. For example, acellular tissue matrix may be produced from any collagen-containing soft tissue and muscular skeleton (e.g., dermis, fascia, pericardium, dura, umbilical cords, placentae, cardiac valves, ligaments, tendons, vascular tissue (arteries and veins such as saphenous veins), neural connective tissue, urinary bladder tissue, ureter tissue, or intestinal tissue), as long as the above-described properties are retained by the matrix.

While an acellular tissue matrix may be made from one or more individuals of the same species as the recipient of the acellular tissue matrix graft, this is not necessarily the case. Thus, for example, an acellular tissue matrix may be made from porcine tissue and implanted in a human patient. Species that can serve as recipients of acellular tissue matrix and donors of tissues or organs for the production of the acellular tissue matrix include, without limitation, humans, nonhuman primates (e.g., monkeys, baboons, or chimpanzees), pigs, cows, horses, goats, sheep, dogs, cats, rabbits, guinea pigs, gerbils, hamsters, rats, or mice. Of particular interest as donors are animals (e.g., pigs) that have been genetically engineered to lack the terminal α-galactose moiety. For descriptions of appropriate animals see co-pending U.S. application Ser. No. 10/896,594 and U.S. Pat. No. 6,166,288, the disclosures of which are incorporated herein by reference in their entirety.

In some embodiments, a freeze dried acellular tissue matrix is produced from human dermis by the LifeCell Corporation (Branchburg, N.J.) and marketed in the form of small sheets as ALLODERM®. The cryoprotectant used for freezing and drying ALLODERM® is a solution of 35% maltodextrin and 10 mM ethylenediaminetetraacetate (EDTA). Thus, the final dried product contains about 60% by weight acellular tissue matrix and about 40% by weight maltodextrin. The LifeCell Corporation also makes an analogous product made from porcine dermis (designated XENODERM) having the same proportions of acellular tissue matrix and maltodextrin as ALLODERM®.

As an alternative to using such genetically engineered animals as donors, appropriate tissues and organs can be treated, before or after decellularization, with the enzyme α-galactosidase, which removes terminal α-galactose (α-gal) moieties from saccharide chains on, for example, glycoproteins. Methods of treating tissue with α-galactosidase to remove these moieties are described in, for example, U.S. Pat. No. 6,331,319, the disclosure of which is incorporated herein by reference in its entirety.

In an implementation, either before or after the cells are killed in the acellular tissue matrix, the collagen-containing material is subjected to in vitro digestion of the collagen-containing material with one or more glycosidases, and particularly galactosidases, such as α-galactosidase. In particular, α-gal epitopes are eliminated by enzymatic treatment with α-galactosidases.

The N-acetyllactosamine residues are epitopes that are normally expressed on human and mammalian cells and thus are not immunogenic. The in vitro digestion of the collagen-containing material with glycosidases may be accomplished by various methods. For example, the collagen-containing material can be soaked or incubated in a buffer solution containing glycosidase. Alternatively, a buffer solution containing the glycosidase can be forced under pressure into the collagen-containing material via a pulsatile lavage process.

Elimination of the α-gal epitopes from the collagen-containing material may diminish the immune response against the collagen-containing material. The α-gal epitope is expressed in non-primate mammals and in New World monkeys (monkeys of South America) as well as on macromolecules such as proteoglycans of the extracellular components. U. Galili et al., J. Biol. Chem. 263: 17755 (1988). This epitope is absent in Old World primates (monkeys of Asia and Africa and apes) and humans, however. Id. Anti-gal antibodies are produced in humans and primates as a result of an immune response to α-gal epitope carbohydrate structures on gastrointestinal bacteria. U. Galili et al., Infect. Immun. 56: 1730 (1988); R. M. Hamadeh et al., J. Clin. Invest. 89: 1223 (1992).

Since non-primate mammals (e.g., pigs) produce α-gal epitopes, xenotransplantation by injection of collagen-containing material from these mammals into primates often results in rejection because of primate anti-Gal binding to these epitopes on the collagen-containing material. The binding results in the destruction of the collagen-containing material by complement fixation and by antibody dependent cell cytotoxicity. U. Galili et al., Immunology Today 14: 480 (1993); M. Sandrin et al., Proc. Natl. Acad. Sci. USA 90: 11391 (1993); H. Good et al., Transplant. Proc. 24: 559 (1992); B. H. Collins et al., J. Immunol. 154: 5500 (1995). Furthermore, xenotransplantation results in major activation of the immune system to produce increased amounts of high affinity anti-gal antibodies. Accordingly, the substantial elimination of α-gal epitopes from cells and from extracellular components of the collagen-containing material, and the prevention of re-expression of cellular α-gal epitopes can diminish the immune response against the collagen-containing material associated with anti-gal antibody binding to α-gal epitopes.

Acellular tissue matrix's suitable for use in the present disclosure can be produced by a variety of methods, so long as their production results in matrices with the above-described biological and structural properties. In general, the steps involved in the production of an acellular tissue matrix include harvesting the tissue from a donor e.g., a human cadaver or any of the above-listed mammals), chemical treatment so as to stabilize the tissue and avoid biochemical and structural degradation together with, or followed by, cell removal under conditions that similarly preserve biological and structural function. The initial stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution may contain an appropriate buffer, one or more antioxidants, one or more oncotic agents, one or more antibiotics, one or more protease inhibitors, and in some cases, a smooth muscle relaxant. In some exemplary embodiments, the harvested tissue (e.g. dermal tissue) is treated with a chemical de-epithelialization solution to remove the epithelium from the tissue sample. For instance, in some embodiments, a sample comprising human or porcine dermal tissue is soaked overnight in 1 M NaCl solution at room temperature to remove the epithelial layer. In certain embodiments, the concentration of the NaCl solution is increased to 1.5 M to ensure complete removal of the epithelial layer.

The tissue is then placed in a decellularization solution to remove viable cells (e.g., epithelial cells, endothelial cells, smooth muscle cells, and fibroblasts) from the structural matrix without damaging the basement membrane complex or the biological and structural integrity of the collagen matrix. The decellularization solution may contain an appropriate buffer, salt, an antibiotic, one or more detergents (e.g., TRITON X-100™, sodium deoxycholate, polyoxyethylene (20) sorbitan mono-oleate), one or more agents to prevent cross-linking, one or more protease inhibitors, and/or one or more enzymes. In some embodiments, the decellularization solution comprises 1% TRITON X-100™ in RPMI media with Gentamicin and 25 mM EDTA (ethylenediaminetetraacetic acid). In some embodiments, the tissue is incubated in the decellularization solution overnight at 37° C. with gentle shaking at 90 rpm. In certain embodiments, additional detergents may be used to remove fat from the tissue sample. For example, in some embodiments, 2% sodium deoxycholate is added to the decellularization solution for the treatment of peritoneal membranes.

After the decellularization process, the tissue sample is washed thoroughly with saline. In some exemplary embodiments, e.g., when xenogenic material is used, the decellularized tissue is then treated overnight at room temperature with a deoxyribonuclease (DNase) solution. In some embodiments, the tissue sample (e.g. peritoneum and pericardial tissue) is treated with a DNase solution prepared in DNase buffer (20 mM HEPES (4-(2-hydroxyethyl)-1-piperazineethanesulfonic acid), 20 mM $CaCl_2$ and 20 mM $MgCl_2$). Optionally, an antibiotic solution (e.g., Gentamicin) may be added to the DNase solution.

After washing the tissue thoroughly with saline to remove the DNase solution, the tissue sample may be subjected to one or more enzymatic treatments to remove any immunogenic antigens if present in the sample. As noted earlier, the tissue sample may be treated with an α-galactosidase enzyme to eliminate α-gal epitopes if present in the tissue. In some embodiments, the tissue sample is treated with α-galactosidase at a concentration of 300 U/L prepared in 100 mM phosphate buffer at pH 6.0 In other embodiments, the concentration of α-galactosidase is increased to 400 U/L for adequate removal of the α-gal epitopes from the harvested tissue (for example, in the treatment of porcine-derived dermal tissues).

After thorough removal of dead and/or lysed cell components, and antigens that may cause inflammation as well as any bioincompatible cell-removal agents, the matrix can be treated with a cryopreservation agent and cryopreserved and, optionally, freeze dried, again under conditions necessary to maintain the described biological and structural properties of the matrix. After cryopreservation or freeze-drying, the acellular tissue matrix can be thawed or rehydrated, respectively. All steps are generally carried out under aseptic, preferably sterile, conditions.

After the acellular tissue matrix is formed, histocompatible, viable cells may optionally be seeded to the acellular tissue matrix to produce a graft that may be further remodeled by the host. In one embodiment, histocompatible viable cells may be added to the matrices by standard in vitro cell co-culturing techniques prior to transplantation, or by in vivo repopulation following transplantation. In vivo repopulation can be by the recipient's own cells migrating into the acellular tissue matrix or by infusing or injecting cells obtained from the recipient or histocompatible cells from another donor into the acellular tissue matrix in situ.

The cell types chosen for reconstitution may depend on the nature of the tissue or organ to which the acellular tissue matrix is being remodeled. For example, endothelial cell is important for the reconstitution of vascular conduits. Such cells line the inner surface of the tissue, and may be expanded in culture. The endothelial cells may be derived directly from the intended recipient patient or from umbilical arteries or veins, and can be used to reconstitute an acellular tissue matrix and the resulting composition grafted to the recipient. Alternatively, cultured (autologous or allogeneic) cells can be added to the acellular tissue matrix. Such cells can be, for example, grown under standard tissue culture conditions and then added to the acellular tissue matrix. In another embodiment, the cells can be grown in and/or on an acellular tissue matrix in tissue culture. Cells grown in and/or on an acellular tissue matrix in tissue culture can be obtained directly from an appropriate donor (e.g., the intended recipient or an allogeneic donor) or they can be first grown in tissue culture in the absence of the acellular tissue matrix.

The following examples are provided to better explain the various embodiments and should not be interpreted in any way to limit the scope of the present disclosure.

Example 1. Functional Study of Vascular Grafts Derived from Dermal Matrices

Vascular grafts were formed using ALLODERM®, which is a human acellular dermal matrix (HADM) available from LifeCell Corporation (Branchburg, N.J.). The HADM was provided in sheets having a thickness between 0.3-0.5 mm. The HADM was soaked in saline solution for 30 min and then cut into 0.5×1.5 cm section. ALLODERM® HADM includes an intact basement membrane, and the HADM sections were rolled into tubes with the basement membrane along the luminal surface of the tube. The tubes were sutured along the joining edge so as to create a single layer tube construct.

The vascular grafts were then tested in a rat abdominal aorta replacement model. Twenty adult (9-11 weeks old) male Lewis rats were anesthetized with intraperitoneal pentobarbital 40 mg/kg, and a midline abdominal incision was formed in each rat. A 1-cm segment of the abdominal aorta, from below the renal arteries to just above the aortic bifurcation, was excised through the midline incision. The excised arterial segment was replaced with a HADM-derived vascular graft. The grafts were implanted in the orthotopic position with end-to-end anastomoses using 9-0 nylon interrupted sutures. The quality of the graft and the extent of healing of the implantation site was recorded at four study end-points (1, 3, 6 and 12 months). Five animals were sacrificed at each endpoint. 1-cm of the vascular graft and 0.5 cm of host tissue material beyond the anastomoses (total explant length of 2-cm) were excised from each sacrificed animal, along with a sample of the spleen and lymph node. The explanted sections were used for histology, immunohostichemistry, SEM (Scanning Electron Microscopy) and TEM (Transmission Electron Microscopy) analyses. The excised samples, representing the graft mid-portion and graft-host tissue interface, were placed in 10% formalin or 8% Glutaraldehyde (for SEM & TEM analysis) for fixation and subsequent analysis.

Clinical Observation

All animals that received the vascular graft had normal post-surgical recovery and either maintained or gained weight during the study period, similar to non-operated animals. Fourteen animals survived to their predetermined sacrifice date with no clinical indication of implant failure as evidenced by limitation of leg movement and pathological changes in the legs. One animal died at four days post-implantation due to internal bleeding. There was no evidence of infection at the surgical site in any animal during the study. Gross observation of the explanted vascular grafts showed no evidence of stenosis, aneurysm, hyperplasia, suture dehiscence or thrombus formation. Additionally, most of the explanted grafts had smooth luminal surfaces and no evidence of calcification was observed. Two of the grafts (explanted at 6 and 12 months) showed areas more rigid than normal vascular structure, suggesting vascular calcification. All of the grafts were well integrated with the native rat aorta at the site of anastomoses.

Histology

Figure 4A:
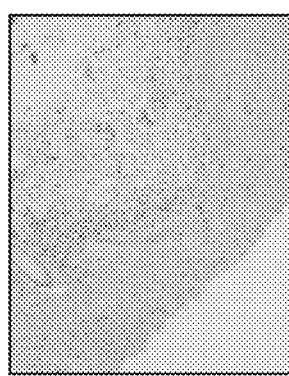
FIGS. 4A-4H are images of histological sections of explanted vascular grafts stained with hemotoxylin and eosin, as described in Example 1.
Figure 4B:
Figure 4C:
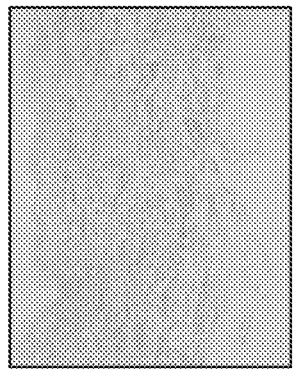
Figure 4D:
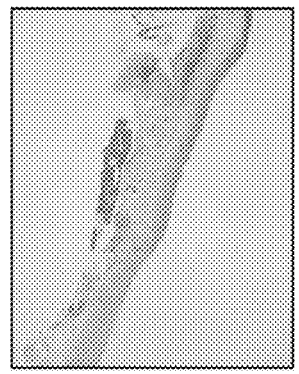
Figure 4E:
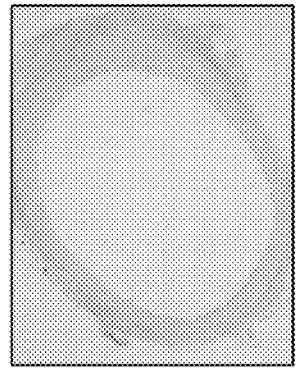
Figure 4F:
Figure 4G:
Figure 4H:

The explanted graft sections were processed with H&E (Hematoxylin and Eosin) and Verhoeff Van Geison staining. H&E staining of a representative graft cross-section at 3-months (FIGS. 4A and 4B) and 12-months (FIGS. 4C-4G) demonstrated fibroblast cells populating the grafts and a few endothelial cells lining the luminal surface of the grafts. FIGS. 4A-4E are H&E stained cross-sections taken at the mid-portion of the grafts, FIGS. 4F and 4G are H&E stained of cross-sections taken at the site of anastomoses, and FIG. 4H is an H&E stained of a graft that was never implanted and was used as a control in the study.

Histology of the explanted anastomosis site showed complete tissue integration and smooth transition of the graft to host blood vessel. A mild inflammatory cell infiltration was observed at 1-month, but the level diminished over time, and no inflammatory cells were observed at 3-months, indicating that no chronic inflammation was induced by the implanted grafts.

Figure 5A:
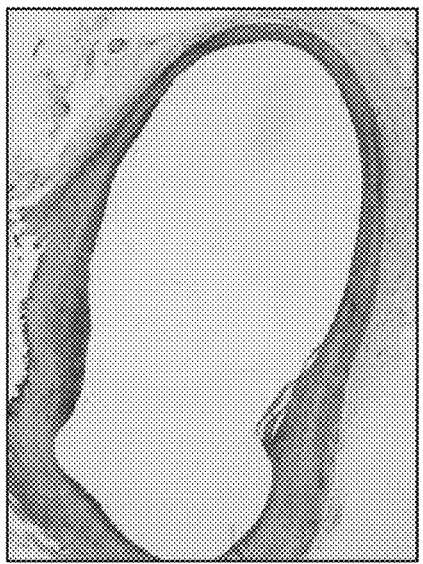
FIGS. 5A-5F are images of histological sections of explanted vascular grafts stained with Verhoeff Van Geison stain, as described in Example 1.
Figure 5B:
Figure 5C:
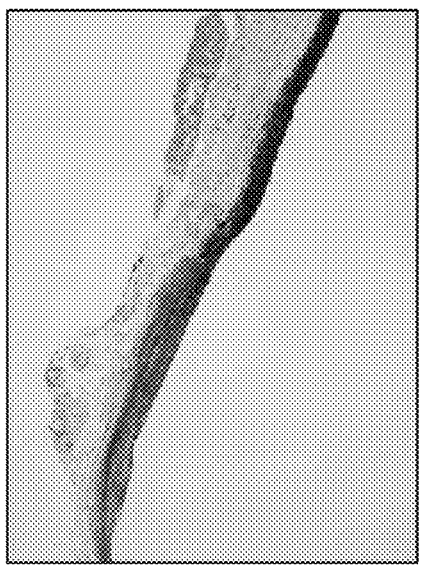
Figure 5D:
Figure 5E:
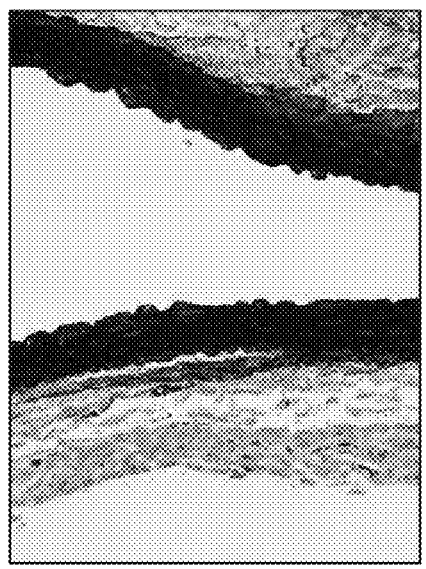
Figure 5F:
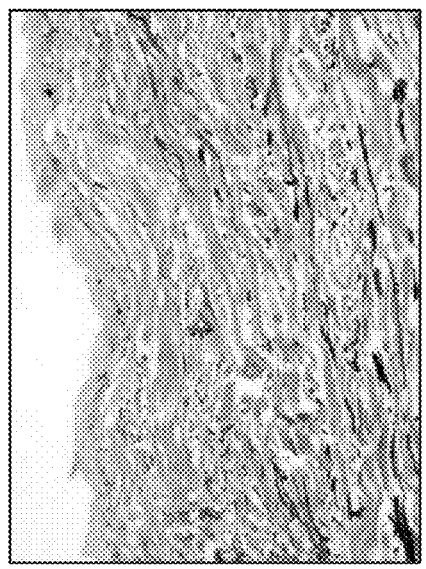

FIGS. 5A and 5B show Verhoff's staining of cross-sections taken at the mid-portion of the grafts, FIGS. 5C and 5D show Verhoff's staining of cross-sections taken at the site of anastomosis, FIG. 5E shows Verhoff's staining of a normal rat aorta and FIG. 5F shows a pre-implant vascular graft used as a control. Verhoff's staining of the graft cross-sections indicated that the neomedia was rich in collagen, and cells appeared to have extensive elastin deposition.

SEM and TEM Analyses

Figure 6A:
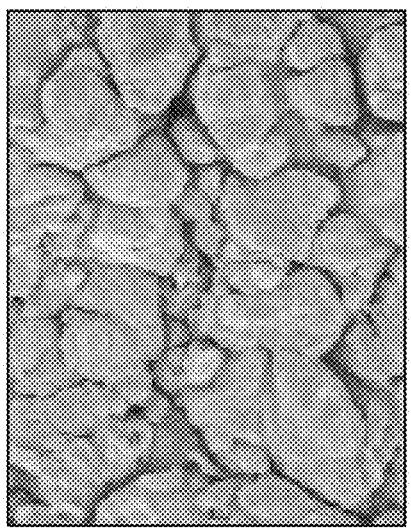
FIGS. 6A-6F are scanning electron micrographs of explanted vascular grafts, as described in Example 1.
Figure 6B:
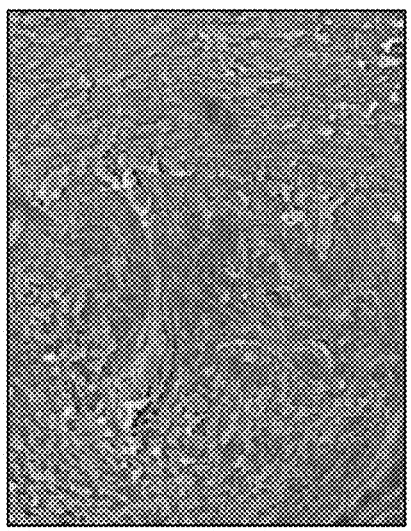
Figure 6C:
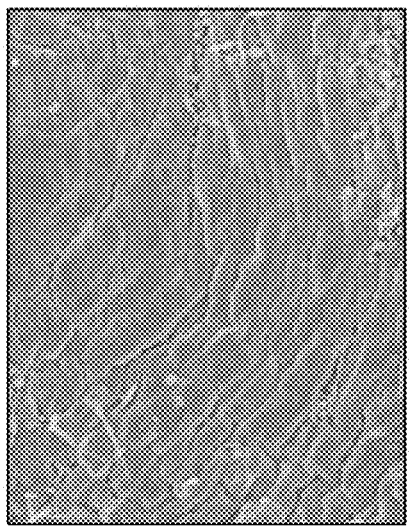
Figure 6D:
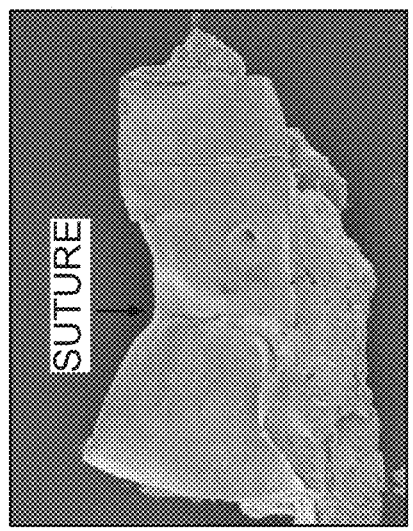
Figure 6E:
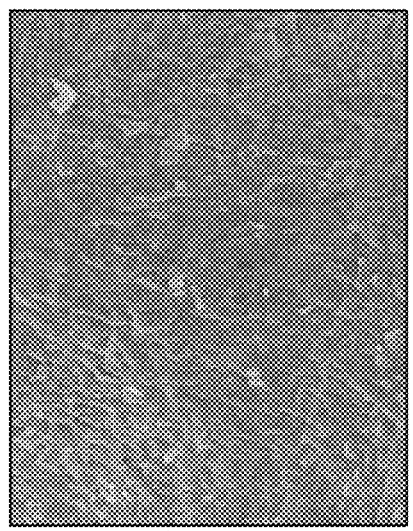
Figure 6F:
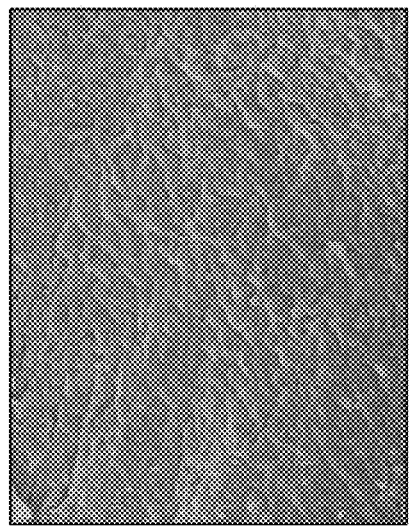

FIGS. 6A-6F are SEM micrographs of vascular grafts produced as described above. SEM of pre-implant grafts showed no cell structures on the surface of the basement membrane, as shown in FIG. 6A. Vascular grafts explanted at 1-month had endothelial cells on their luminal surfaces (FIG. 6B), and at 3-month endothelial-type cells completely covered the luminal surface (FIG. 6C). The interface of the graft and the rat aorta showed intact anastomosis, as shown in FIG. 6D. The surface of the graft at 3-months (FIG. 6E) was completely covered with cells and was indistinguishable from the surface of the rat aorta (FIG. 6F).

Figure 7B:
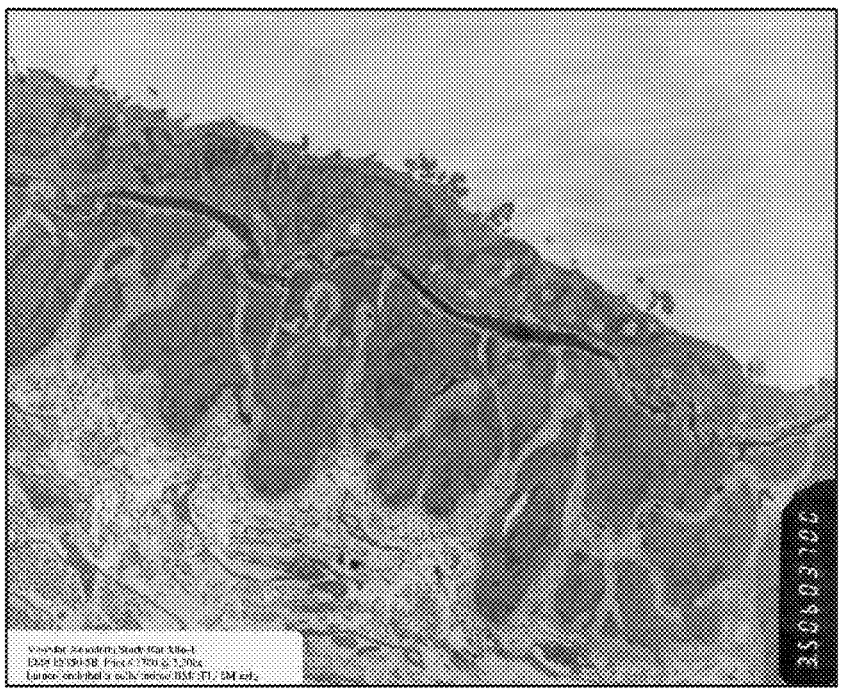
FIGS. 7A and 7B are transmission electron micrographs of an explanted vascular graft and a rat aorta, as described in Example 1.
Figure 7A:
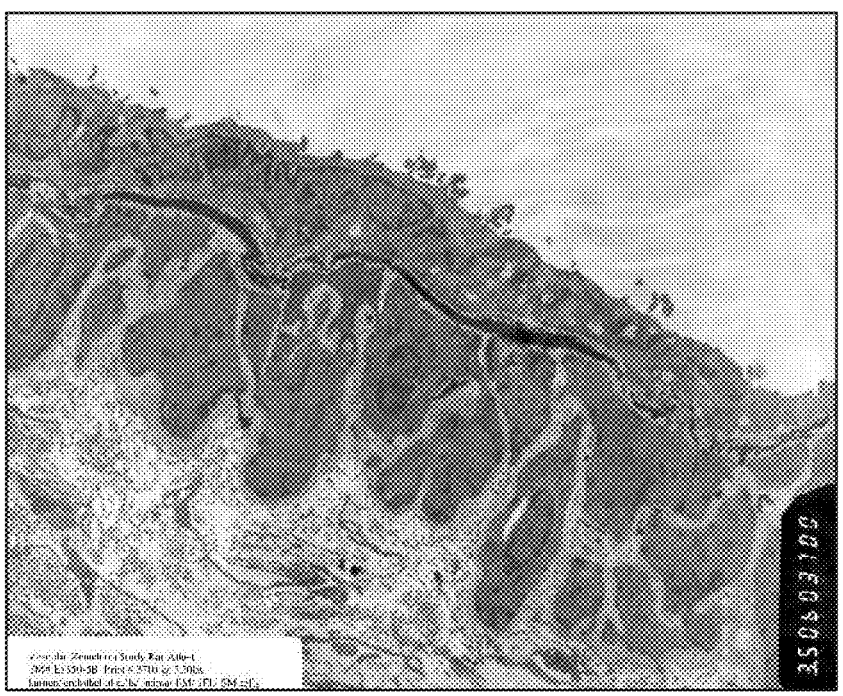

Similarly, TEM micrographs of representative vascular grafts taken at 1-month (FIG. 7A) showed flat endothelial cells with accompanying basement membrane (BM) lining the lumen of the graft. Smooth muscle cells (SMC) with microfilaments and dense bodies were also clearly seen on the TEM images. The dark staining material along the surface of the smooth muscle cells, which is representative of elastic fiber formation, was observed on the TEM micrographs, although the elastic fibers formed were immature compared to the internal elastic lamina (IEL) observed in the TEM image of normal rat aorta (FIG. 7B).

Immunostaining

Figure 8D:
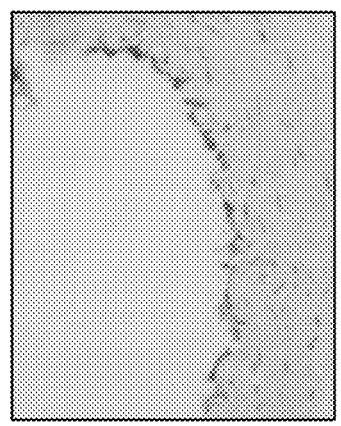
FIGS. 8A-8D are images of histological sections of explanted vascular grafts stained with antibodies against endothelial cells, as described in Example 1.
Figure 8C:
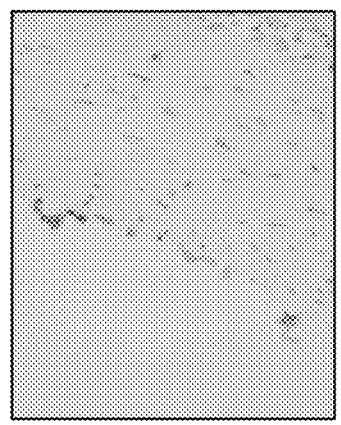
Figure 8B:
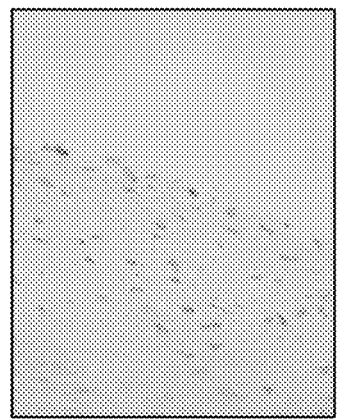
Figure 8A:
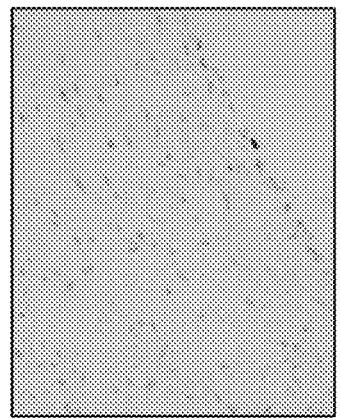
Figure 8H:
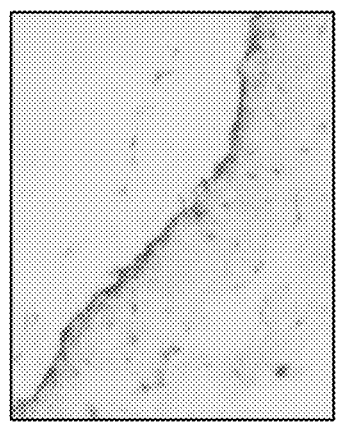
FIGS. 8E-8H are images of histological sections of explanted vascular grafts stained with antibodies against von Willebrand Factor, as described in Example 1.
Figure 8G:
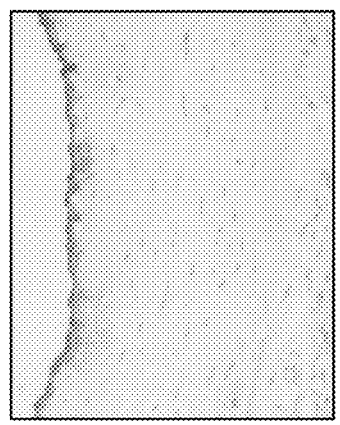
Figure 8F:
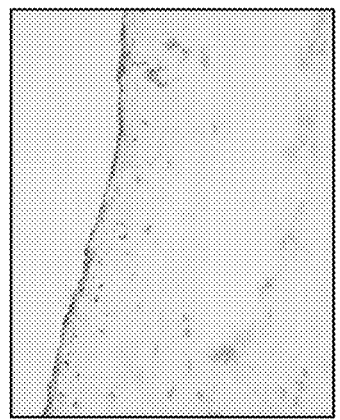
Figure 8E:
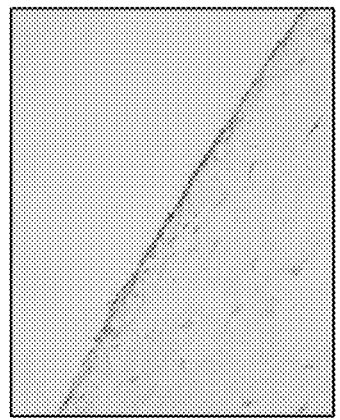
Figure 10A:
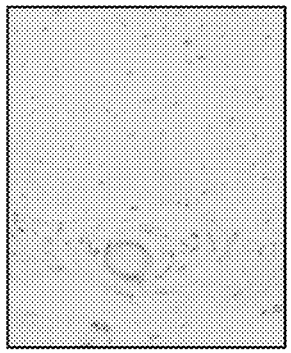
FIGS. 10A-10L are images of histological sections of explanted vascular grafts stained with antibodies against rat T-cell, B cell and macrophage, as described in Example 1.
Figure 10B:
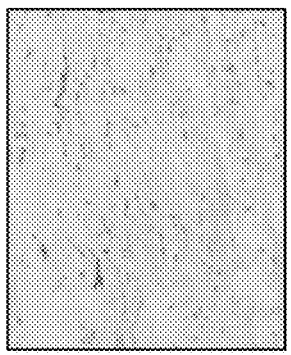
Figure 10C:
Figure 10D:
Figure 10E:
Figure 10F:
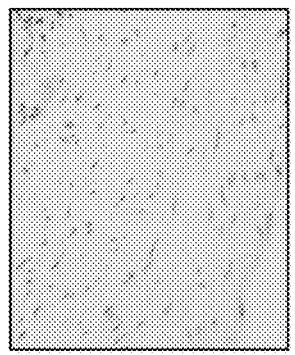
Figure 10G:
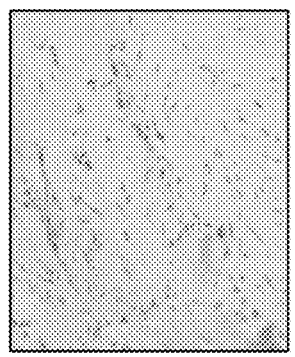
Figure 10H:
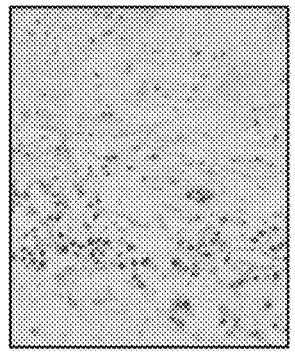
Figure 10I:
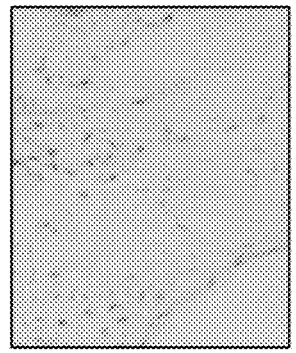
Figure 10J:
Figure 10K:
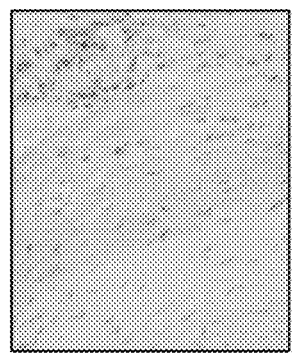
Figure 10L:
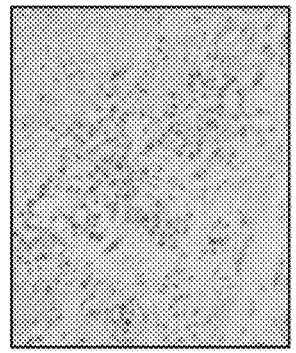

Endothelial cell development on the luminal surface of the grafts was confirmed using endothelial cell staining and vWF (von Willebrand Factor) staining. Specific antibodies against rat endothelial cells and vWF were used to identify endothelial cell deposition on the surface of the lumen. Endothelial cells were observed at 1-month, but did not fully cover the lumen, as shown in FIG. 8A. Significant deposition of endothelial cells was observed at 3-months, 6-months and 12-months, as shown in FIGS. 8B, 8C and 8D, respectively. Immunohistological staining by vWF showed that the entire surface of the graft was lined with endothelium, as shown in FIGS. 8E-8H.

Repopulation of the vascular graft with smooth muscle cells and fibroblast cells was verified by staining with specific antibodies against α-smooth muscle actin and vimetin, respectively. Cross-sections of rat abdominal aorta were also stained with antibodies against α-smooth muscle actin and fibroblast cells for use as control (FIGS. 9A and 9F, respectively). The grafts at 1-month (FIGS. 9B and 9G), 3-months (FIGS. 9C and 9H), 6-months (FIGS. 9D and 9I) and 12-months (FIGS. 9E and 9J) showed repopulation of the graft with smooth muscle cells and fibroblast cells starting at 1 month post-implantation.

Inflammatory and Immune Response

The explanted sections were stained with anti-rat T cell, B cell and macrophage antibodies to identify the inflammatory response of the host against the implanted graft. FIGS. 10A-10D represent grafts stained with anti-rat T cell antibodies at 1-month, 3-months, 6-months and 12-months, respectively. Similarly, FIGS. 10E-10H represent grafts stained with B cell antibodies, and FIGS. 10I-10L represent grafts stained with antibodies against macrophages. All three types of inflammatory cells were found to infiltrate the implanted grafts moderately at 1-month, but no inflammatory cell infiltration was detected in the neomedia. Inflammatory cells diminished significantly at 3-months, and those that were observed were primarily near the periphery of the graft. No inflammatory cells were observed after 6 months.

Similarly, a moderate level of IgG antibody was seen on the grafts during the first 3 months, but not in the neomedia. Rat IgG (FIGS. 11A-11E) and IgM (FIGS. 11F-11J) bound to the vascular grafts were examined at 1-month (FIGS. 11A and 11F), 3-months (FIGS. 11B and 11G), 6-months (FIGS. 11C and 11H) and 12-months (FIGS. 11D and 11I). Normal rat abdominal aorta (FIGS. 11E and 11J) was used as a control. As shown in FIGS. 11A-11D, moderate level of antibody IgG was discovered on the graft during the first 3 months. After 3-months, the IgG level diminished significantly. IgM deposition was not found in any graft during the study.

Example 2. Assessment of Mechanical Strength, Thermostability and Thrombotic Effect of Vascular Grafts Formed Using Bioadhesives Vascular grafts derived from human acellular dermal matrix (HADM) were used for this study. Sheets of HADM were rolled into tubular constructs, and the edges of the sheet were attached using fibrin glue. The burst strength of the grafts was evaluated using burst test (American National Institute of Standards (ANSI) code: ANSI/AAMI/ISO 7198: 1998/2001/®2004). The maximum burst strength was calculated to be 1639±432 mmHg (n=2), which indicated that the vascular grafts formed using bioadhesives were strong enough to sustain physiological blood pressures.

Figure 12:
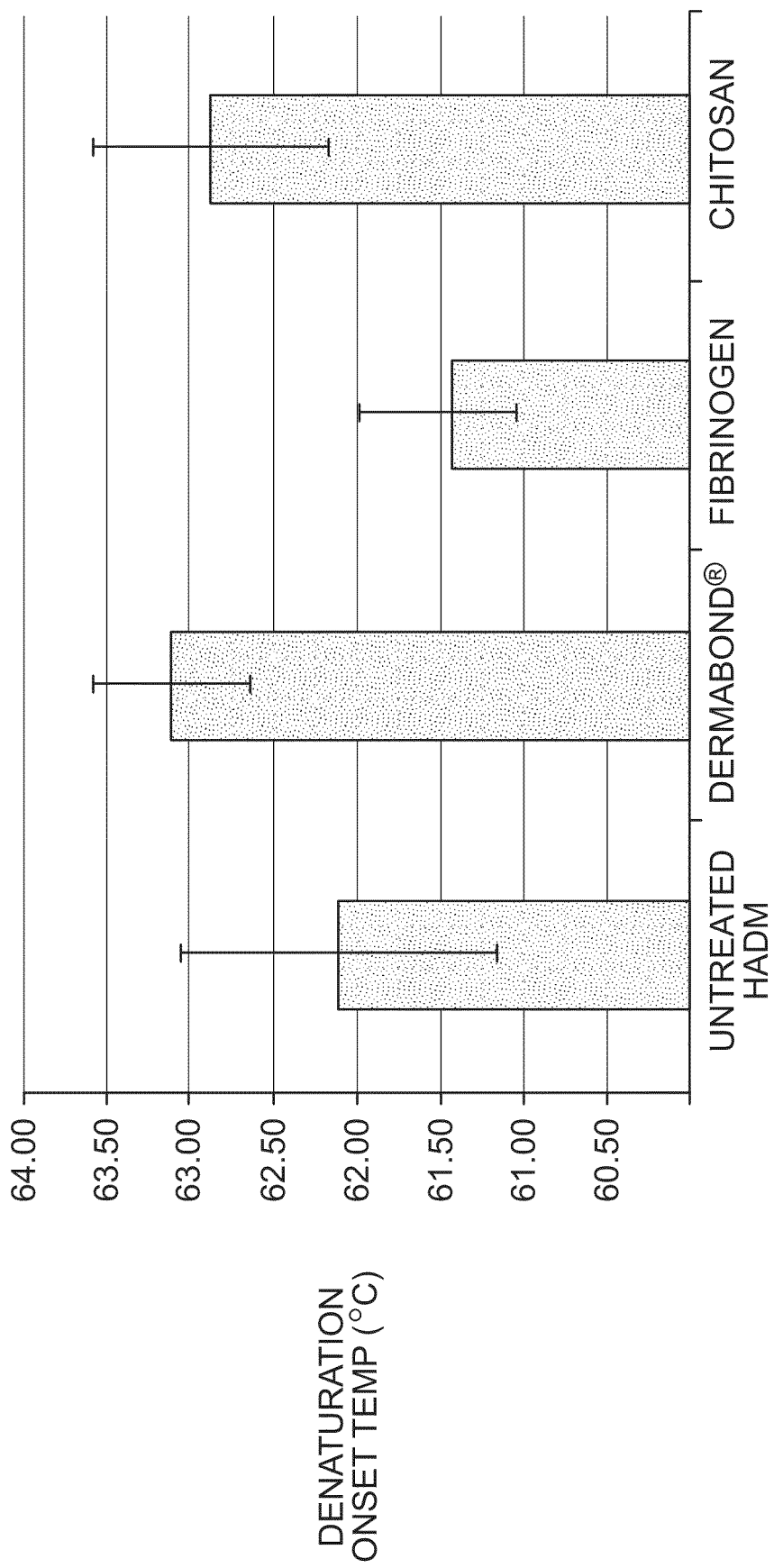
FIG. 12 shows the thermostability results of glued acellular dermal matrices, as described in Example 2.

The denaturation onset temperatures of collagen in the dermal matrices was determined by Differential Scanning Calorimetry (DSC). As shown in the graph in FIG. 12, the collagen denaturation temperature of the glued vascular grafts compared favorably with that of human acellular dermal matrices. The graph includes data that corresponds to denaturation onset temperature of untreated HADM, and vascular grafts formed by gluing HADM with DERMA-BOND®, fibrinogen and chitosan-based adhesives. Data from this experiment indicates that the bioadhesives did not alter the biochemical properties of the matrix.

Figure 13:
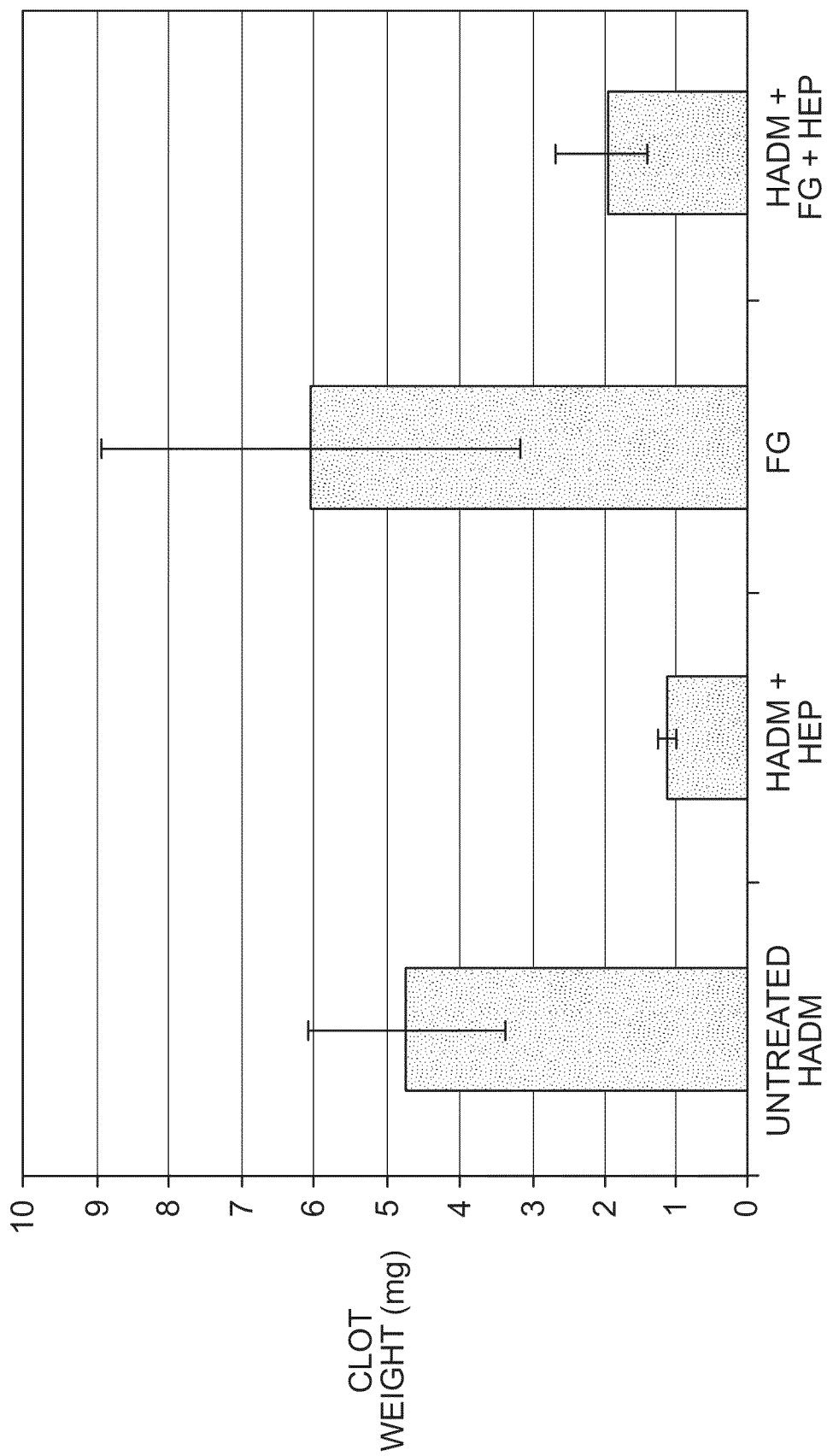
FIG. 13 illustrates the effect of bioglues on the antithrombotic property of heparin coated on acellular dermal matrices, as described in Example 2.

The efficacy of antithrombotic agents (e.g. heparin) on glued vascular grafts was assessed using a clot forming method. Heparin coating was performed by suspending the vascular grafts in a 0.4% heparin sodium salt solution for 24 hours at room temperature. 200 µl of blood and 12.5 µl of 100 mM $CaCl_2$ were added to the luminal surface of 1 $cm^2$ sections of the vascular grafts, and the graft sections were then placed in an incubator for 1 hour at 37° C. with 5% $CO_2$. Any visible clot was removed from the surface with forceps, placed in a tube, lyophilized, and weighed. As shown in the graph in FIG. 13, the antithrombotic property of heparin is not affected when heparin came in contact with a bioadhesive. The graph includes data that corresponds to weight of blood clots formed on untreated HADM, heparin treated HADM (HADM+Hep), fibrinogen glue (FG) and HADM treated with both heparin and fibrinogen glue (HADM+FG+Hep). As shown in the graph, the amount of blood clot formed on HADM treated with both heparin and fibrinogen glue compared favorably with the blood clot data from the heparin treated HADM, indicating that the fibrinogen glue did not interfere with the antithrombotic function of the heparin coating on dermal matrices.

The invention claimed is:
1. A vascular graft, comprising:
   an anticoagulant;
   a tubular conduit having a lumen for the passage of blood therethrough wherein the tubular conduit consists essentially of a single sheet of dermal acellular tissue matrix having a basement membrane, the basement membrane disposed along an inner surface of the lumen and the single sheet forming a single layer wall around the lumen; and
   an adhesive comprising fibrinogen attaching a first longitudinal edge of the acellular tissue matrix to a second longitudinal edge of the acellular tissue matrix to form a fluid-tight seam extending along a length of the vascular graft.

2. The vascular graft of claim 1, wherein attaching the first and the second longitudinal edges with the adhesive creates a longitudinal ridge protruding from an abluminal surface of the tubular wall.

3. The vascular graft of claim 1, wherein the first and the second longitudinal edges are attached using a combination of sutures and the adhesive.

4. The vascular graft of claim 1, wherein the dermal matrix is derived from human skin.

5. The vascular graft of claim 1, wherein the acellular tissue matrix is derived from tissue that is xenogeneic to a human recipient.

6. The vascular graft of claim 5, wherein the tissue is from an 1,3-galactosyltransferase ($\alpha$1,3GT) deficient pig.

7. The vascular graft of claim 1, wherein the acellular tissue matrix is derived from tissue that is allogeneic to a human recipient.

8. The vascular graft of claim 1, wherein the anticoagulant comprises heparin.

* * * * *